US006342701B1

(12) United States Patent
Kash

(10) Patent No.: US 6,342,701 B1
(45) Date of Patent: Jan. 29, 2002

(54) TIME CORRELATED PHOTON COUNTING

(75) Inventor: Jeffrey A. Kash, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/349,310

(22) Filed: Jul. 8, 1999

(51) Int. Cl.⁷ .............................................. G01N 21/64
(52) U.S. Cl. ................................................... 250/458.1
(58) Field of Search ........................ 250/458.1, 361 R, 250/362, 459.1, 461.1, 461.2, 365, 369; 356/318

(56) References Cited

U.S. PATENT DOCUMENTS

| 3,676,783 A | | 7/1972 | Kinbara et al. | |
|---|---|---|---|---|
| 4,179,664 A | | 12/1979 | Bedwell | |
| 4,600,306 A | * | 7/1986 | Hara et al. | 356/317 |
| 4,855,930 A | * | 8/1989 | Chao et al. | 702/32 |
| 5,071,249 A | * | 12/1991 | Takahashi et al. | 356/318 |
| 5,202,744 A | * | 4/1993 | Louis | 356/73 |
| 5,459,323 A | * | 10/1995 | Morgan | 250/458 |
| 5,909,278 A | * | 6/1999 | Deka et al. | 356/318 |
| 5,990,484 A | * | 11/1999 | Ohsuka | 250/458.1 |
| 6,140,048 A | * | 10/2000 | Müller et al. | 435/6 |

OTHER PUBLICATIONS

G. Hungerford, et al. "Single–photon timing detectors for fluorescence lifetime spectroscopy", Meas. Sci. Technol. 7 (1996), pp. 121–135.

S. Cova, et al. "Constant–fraction circuits for picosecond photon timing with microchannel plate photomultipliers", American Institute of Physics, Rev. Sci. Instrum. 64 (1), Jan. 1993, pp. 118–124.

* cited by examiner

*Primary Examiner*—Constantine Hannaher
*Assistant Examiner*—Albert Gagliardi
(74) *Attorney, Agent, or Firm*—Fleit, Kain, Gibbons, Gutman & Bongini P.L.; Jon A. Gibbons; Casey P. August

(57) ABSTRACT

A system for time-correlated photon counting. The system uses one or more photon detectors to produce electrical pulses corresponding to photons read from a target. The system uses a discriminator with a first input coupled to a trigger output from a pulsed optical source and a second input for receiving the electrical pulses. A time-to-pulse height converter is used for producing a series of difference signals each with a respective maxima and whose magnitude is related to the time difference between the trigger output and the electrical pulses. In addition, the system employs a pulse shaping electronic circuit for receiving pulsed electrical output and producing a series of one or more characteristic signals. An A/D converter with a first input receives the difference signals and a second input receives part of the characteristic signals. The A/D converter produces a first series of digital signals representing the difference signals and a second series of digital signals representing the characteristics signals. The results of the A/D converter are feed to a multichannel analyzer for time-shifting the first series of digital signals based on at the second series of digital signals so that the maxima for any given difference signals occurs at the same time as the maxima for at least one other part of the series of the difference signals.

21 Claims, 4 Drawing Sheets

TIME CORRELATED PHOTON COUNTING

CROSS-REFERENCE TO RELATED APPLICATIONS

Not applicable

BACKGROUND OF THE INVENTION

1. Field of the Invention

The invention disclosed broadly relates to the field of time-resolved photon emission and more particularly relates to the field of fast single photon detection and counting and timing.

2. Description of the Related Art

The use of single photon counting for both analytical tools and research continues to increase. Time correlated photon counting TCPC) (also known as time correlated single photon counting or photon timing) has been known for many years, as described in the article entitled "Single-Photon Timing Detectors For Fluorescence Lifetime Spectroscopy" by Graham Hungerford and David J. S. Birch on pp.121–135 of Measurement Science Technology 7 (1996), printed in the UK. FIG. 1 illustrates a conventional TCPC time correlated single photon detection (SPD) counting system 100. A target 102 to be sampled is placed under a lens 104. A pulsed optical source 120 emits a short pulse of photons which is focused onto a target 102. Note that neither the pulsed optical source 120 nor the target 102 is part of the TCPC system. The source 120 and target 102 are present here for the well-known purpose of calibrating and improving the temporal response function of the TCPC system. For this calibration and improvement to be effective, the duration of this photon pulse should be much less than the temporal response function of the TCPC system. A detector 106 reads photon emissions elastically scattered from the target 102 as focused by lens 104. The detector 106 produces an electrical pulse corresponding to each of the photons read from the target 102. The pulsed optical source 120 also provides an electrical trigger pulse (synchronous with each optical pulse) 110 to an input 112 of a timing discriminator and time-to-pulse height converter, hereinafter converter 108. The converter 108 provides to output 114 a series of difference signals each of which is an analog electrical pulse with a respective maximum and whose magnitude is related to the time difference detected by converter 108 between the trigger 110 and the electrical pulses from detector 106 corresponding to a detected photon of the optical pulse associated with the trigger 110. An analog-to-digital (A/D) converter 116 converts the analog signal output 114 from the converter 108 to a digital signal for use by a 1-dimensional multichannel analyzer 1-D MCA 118. The 1-D MCA 118 displays the temporal response function of the apparatus to the pulsed optical source 120.

The principle of operation, performance and application of many of the different types of single-photon timing detectors is described in the article entitled "Single-Photon Timing Detectors For Fluorescence Lifetime Spectroscopy" by Graham Hungerford and David J. S. Birch on pp. 121–135 of Measurement Science Technology 7 (1996), printed in the UK. As described in detail by Hungerford and Birch, for any given photon detected, geometrical effects arising from the physical dimensions of the single photon timing detector SPD and the statistical nature of the electron generation and amplification or generation result in an electrical output pulse which can vary in amplitude and shape.

In order to achieve good a temporal response function of minimum width with TCPC, the detector amplifiers and electronics must be able to accurately determine when each detected photon actually struck the photodetector. However, for SPDs, this determination can be difficult because of the variation in the amplitude and the shape of the electrical pulses associated with detected photons. To achieve optimum time resolutions with a given photon detector, many analog triggering techniques have been applied.

One analog triggering technique is described in U.S. Pat. No. 4,179,664 issued Dec. 18, 1979 to Michael O. Bedwell, entitled "Constant Fraction Signal Shaping Apparatus." U.S. Pat. No. 4,179,664 describes a trigger pulse, derived, for instance, from a radiation detector, that is applied to an input circuit which splits the pulse into two components. The respective component signals are acted on by two characteristic circuits, one of which attenuates the first signal component and the other of which delays the second signal component. The respective attenuated signal and delayed signal are applied to a passive element, such as a differential transformer to invert one component with respect to the other and to sum the resulting signals. The output signal of the differential transformer is a constant-fraction bipolar timing signal which is correlated with the time of occurrence of the event identified with the trigger pulse. In order to achieve accurate timing, constant fraction triggering requires that the amplitude of the electrical impulse created by each detected photon can vary, but that the shape of the electrical impulses remains constant. However this a-priori assumption that the shape the electrical pulse created by each detected photon stays constant is only approximately valid for only a very limited range of varying pulse amplitudes. Accordingly, a need exists for a method and apparatus to count and time photons when the electrical pulse shape is variable over a wider range of pulse amplitudes and triggering models.

An alternate approach to achieve optimum time resolution with a given SPD is used in the pico-Timing™ discriminator from EG&G Ortec, Model 9307. The pico-Timing™ discriminator employs conventional edge triggering on the rising edge of the electrical pulse from the SPD. The discriminator attempts to compensate for pulse-to-pulse variations through use of an analog "slewing compensation" circuit which presumes that the slew rate of the rising electrical edge output pulses of the SPD is constant. However, this approximation is valid only over a limited range of pulse amplitudes, and pulses outside this range are not accurately timed. Therefore a need exists for a method and apparatus to provide accurate single photon counting when the slew rates of the SPD is not constant.

At best, the assumption of constant pulse shape or constant slew rate is valid only over a limited range of pulse amplitudes, and pulses outside this range are not accurately timed. To maintain the best timing resolution, pulses outside this range must be rejected. On the other hand, many times the photonic light emitted by photoluminescent or electroluminescent targets which are to be measured by a TCPC measurement apparatus is weak. If a significant fraction of the detected photons needs to be rejected to maintain good timing resolution, the time required to perform a TCPC measurement can become unacceptably long. Accordingly, a need exists for a method and apparatus to provide better time resolution than currently used analog signal processing methods, while not rejecting a significant fraction of detected photons so as to enable measurements of weakly emitting targets or sources. An example of where it is usually not acceptable to reject a significant fraction of detected photons in order to maintain optimum time is described in U.S. patent application Ser. No. 08/683,837 for Picosecond Imaging Circuit Analysis (PICA), now U.S. Pat. No. 5,940,545 and commonly assigned herewith to IBM.

SUMMARY OF THE INVENTION

Briefly, in accordance with the present invention, a system for time—correlated photon counting comprises: at least one photon detector for producing electrical pulses corresponding to photons read from a target; at least one converter comprising: a first input coupled to a trigger output from a pulsed optical source; a second input for receiving the electrical pulses; digital delay measurement apparatus to measure the time difference between the trigger output and the electrical pulses; a digitizer for digitizing at least one criterion related to the electrical pulse; an interface to a storage device for storing the digital delay measurements and for storing the digitized criterion; and shifter circuit or algorithms for time-shifting at least part of the stored digital delay measurements based on at least part of the stored digitized criterion so that the width of the temporal response function for the system is minimized.

In accordance with another embodiment of the present invention, a method is disclosed for corresponding to the above system.

DETAILED DESCRIPTION OF AN EMBODIMENT

Figure 1:
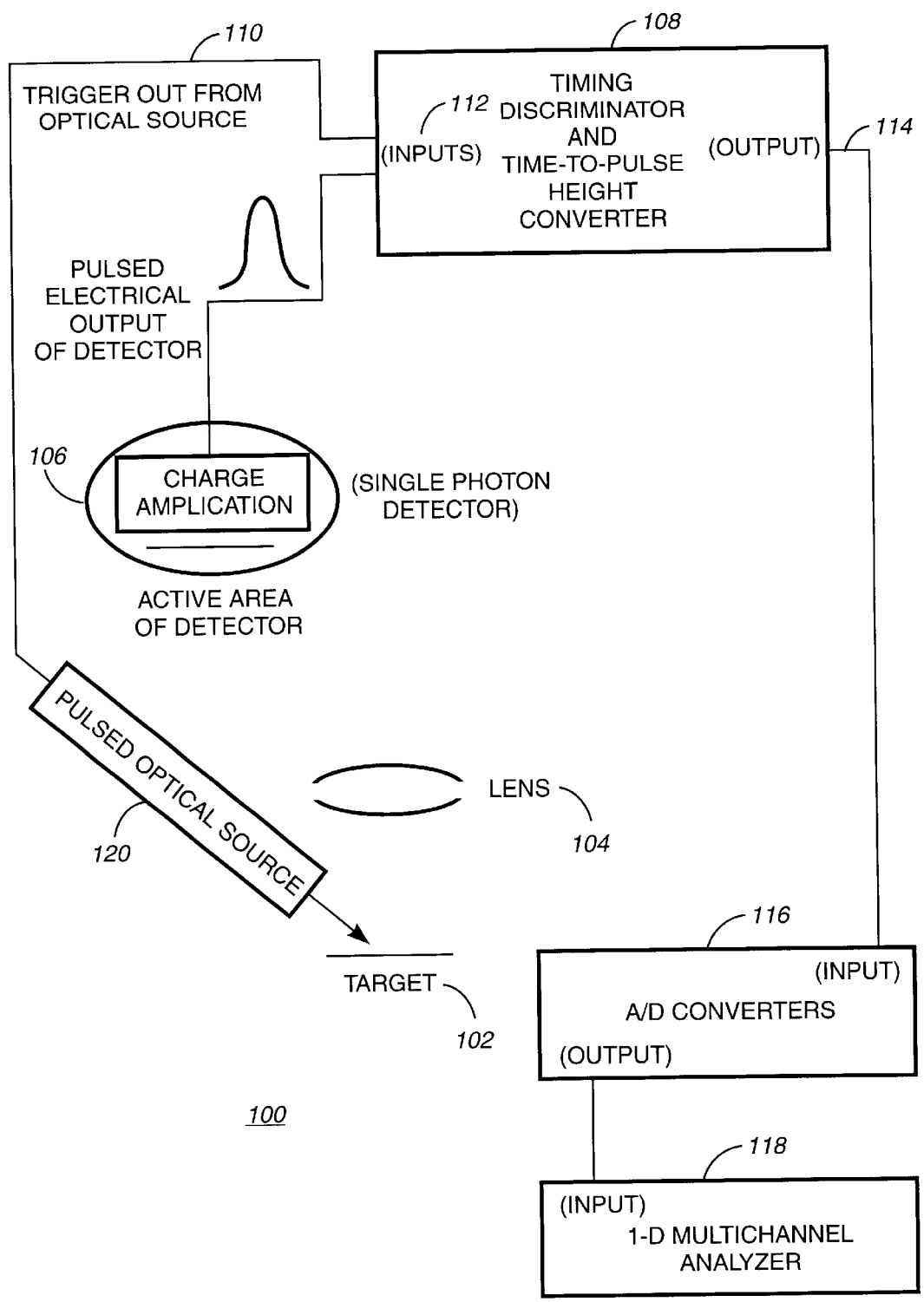
FIG. 1 is a functional block diagram of a typical time correlated photon counting single photon detection apparatus (prior art).
Figure 2:
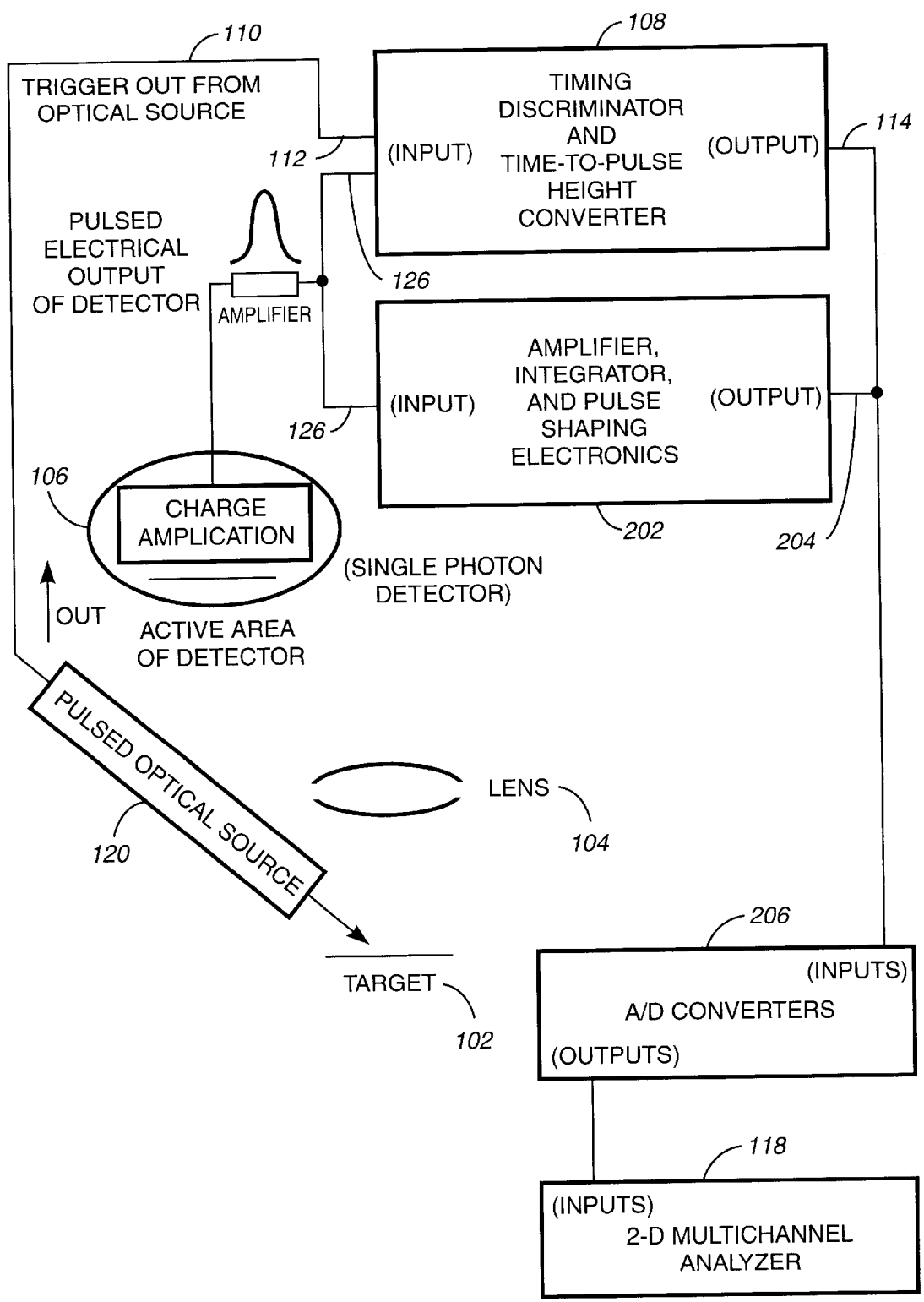
FIG. 2 is a functional block diagram of a time correlated photon counting apparatus and integrated amplitude system using a typical single photon detection system of FIG. 1 with improved timing electronics pulse shaping electronics according to the present invention.

Referring now in more detail to the drawings in which like numerals refer to like parts throughout the several views, FIG. 2 is a functional block diagram of an improved TCPC time and integrated amplitude system 200 using a typical TCPC single photon detection system as system 100 of FIG. 1, with additional electronics according to the present invention. An amplifier, integrator and pulse shaping electronics, hereinafter simply referred to as pulse shaping electronics 202 are placed in a parallel path to converter 108. The pulse shaping electronics 202 has an input 126 which is coupled to the output of the single photon detector SPD 106. An output 204 is coupled to an A/D converter 206. In the system 200 the electrical pulses from each photon as read by detector 106 are characterized by a time difference as described in FIG. 1. The time difference is represented by an analog electrical pulse series of difference signals, each with respective maxima and whose magnitude is related to the time difference between the trigger 110 and the electrical pulses from detector 106. In this specific implementation, the converter 108 is a pico-Timing™ discriminator from EG&G Ortec Model 9307 which has been optimized as taught in the accompanying instruction manual, in combination with a time to pulse height converter, EG&G Ortec Model 457. The pulse shaping electronics 202 consist of the pulse from detector 106 as amplified, integrated, and shaped by an Ortec model 5799 fast amplifier followed by an Ortec model 570 amplifier which amplify, integrate, and shape each electrical pulse from detector 106. The output of the pulse shaping electronics 202 in this embodiment is an electrical pulse whose height is proportional to the integrated area of the electrical pulse from detector 106. It is important to note that other functionally similar electronics, either analog or digital or a combination of analog and digital, may be substituted for the converter 108 and/or the pulse shaping electronics 202 used in place of this discriminator and these amplifiers. For example, the time to pulse height converter could be replaced with a high speed timer which counted a high speed clock to determine the time difference between the trigger 110 and the electrical pulses from detector 106. As another example, the A/D converter 206 could be integrated into its converter 108 to produce an integrated "digital delay measurement apparatus." Similarly, the pulse shaping electronics 202 can be integrated with its A/D converter to produce an integrated "digital pulse area measurement apparatus."

After the outputs of the converter 108 and the pulse shaping electronics 202 are digitized by the A/D converters, a 2-D Multichannel Analyzer, such Model MPAWIN or MPA-3 from FAST ComTec is used to store the digitized pairs. A histogram of the digitized output of converter 108 gives the temporal response function of the conventional TCPC system (i.e., as in FIG. 1). This temporal response function is shown as the "uncorrected" curve in FIG. 4. A histogram of the digitized output of the pulse shaping electronics 202 gives the distribution of the integrated area of the electrical pulses from detector 106, hereinafter referred to as the "pulse amplitude".

Figure 3:
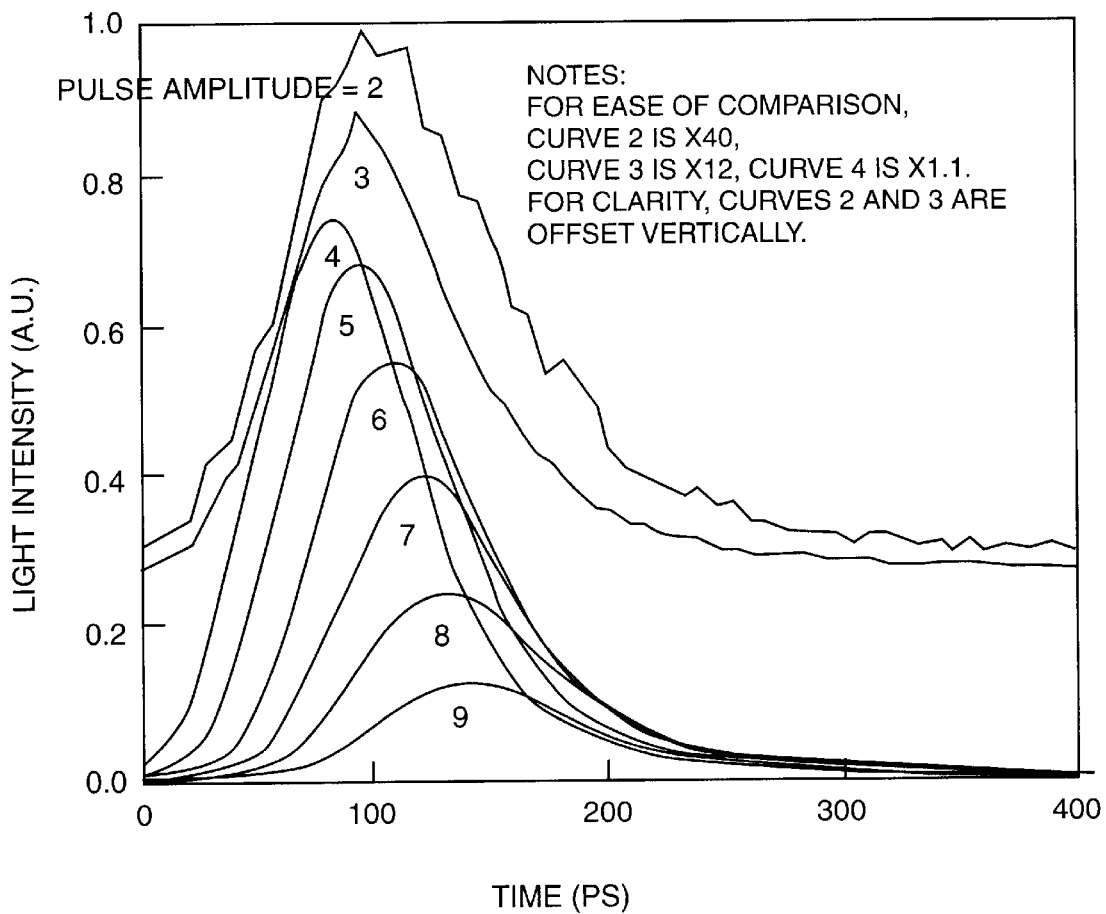
FIG. 3 is a plot for photons detected using the system of FIG. 2, wherein the accepted pulse amplitude of single-photon-derived electrical pulses from the single photon detector was limited to a series of small ranges, one range for each curve, according to the present invention.

Using the pulse amplitude as a filter, more detailed histograms of the output of converter 108 can be plotted, so that a temporal response function of the TCPC system 200 for various ranges of pulse amplitudes are obtained as shown in FIG. 3.

Turning now to FIG. 3, there is illustrated a plot 300 for photons detected using the system 200 of FIG. 2 on a 2-D Multichannel Analyzer according to the present invention. Here, the pulse amplitudes are in arbitrary units, where the maximum pulse amplitude detected has an amplitude of about 10. Each curve in FIG. 3 is labeled with the corresponding "pulse amplitude", which is the same as the first column "pulse amplitude" in Table 1. For example, the pulse amplitude of trace or function or curve 2 in FIG. 3 would fall in the category of pulse amplitude <2.90 in Table 1, while the pulse amplitude =7 curve of FIG. 3 would fall in the pulse amplitude between 6.77 and 7.41 in Table 1 below. The height of each curve in FIG. 3 is not related to the pulse amplitude. The height merely reflects the number of pulses with that specific pulse amplitude range. A key to the present invention is to note that in FIG. 3, the histograms corresponding to pulses of different amplitudes have a maximum at different times, even though the converter 108 has been optimized according to the prior art. The maximum is not a linear function of pulse amplitude. Thus, the most common pulses from the detector 106 (which have a pulse amplitude of about 4) have a maximum at about 83 picoseconds, while a pulse amplitude of 2 or 9, for example, which is relatively uncommon, has a maximum at about 140 picoseconds. In essence, each of the curves of FIG. 3 is the time response of the TCPC time correlated SPD system 200 when it is limited to accepting pulses from the detector of a specific pulse amplitude. However, since each detected photon has both the time of detection and the pulse amplitude stored, it is possible to use curves, such as the plot of FIG. 3 to shift the time of each detected photon based on the pulse amplitude, so that each of the curves in FIG. 3 are shifted to where the maxima occur at precisely the same time. This time shifting improves the temporal response function of the system without dropping any of the detected photons. In the particular case of the data of FIG. 3 where each digital channel of time corresponded to 7.235 picoseconds, the following shifts were applied:

TABLE 1

| PULSE AMPLITUDE | TIME SHIFT (channels) |
| --- | --- |
| <2.90 | 0 |
| 2.90 to 3.44 | −1 |
| 3.44 to 3.96 | −2 |
| 3.96 to 4.50 | −3 |
| 4.50 to 5.16 | −2 |
| 5.16 to 5.66 | −1 |
| 5.66 to 6.25 | 0 |
| 6.25 to 6.77 | 1 |
| 6.77 to 7.41 | 2 |
| 7.41 to 8.07 | 3 |
| 8.07 to 8.67 | 4 |
| 8.67 to 9.46 | 5 |
| >9.46 | 6 |

Figure 4:
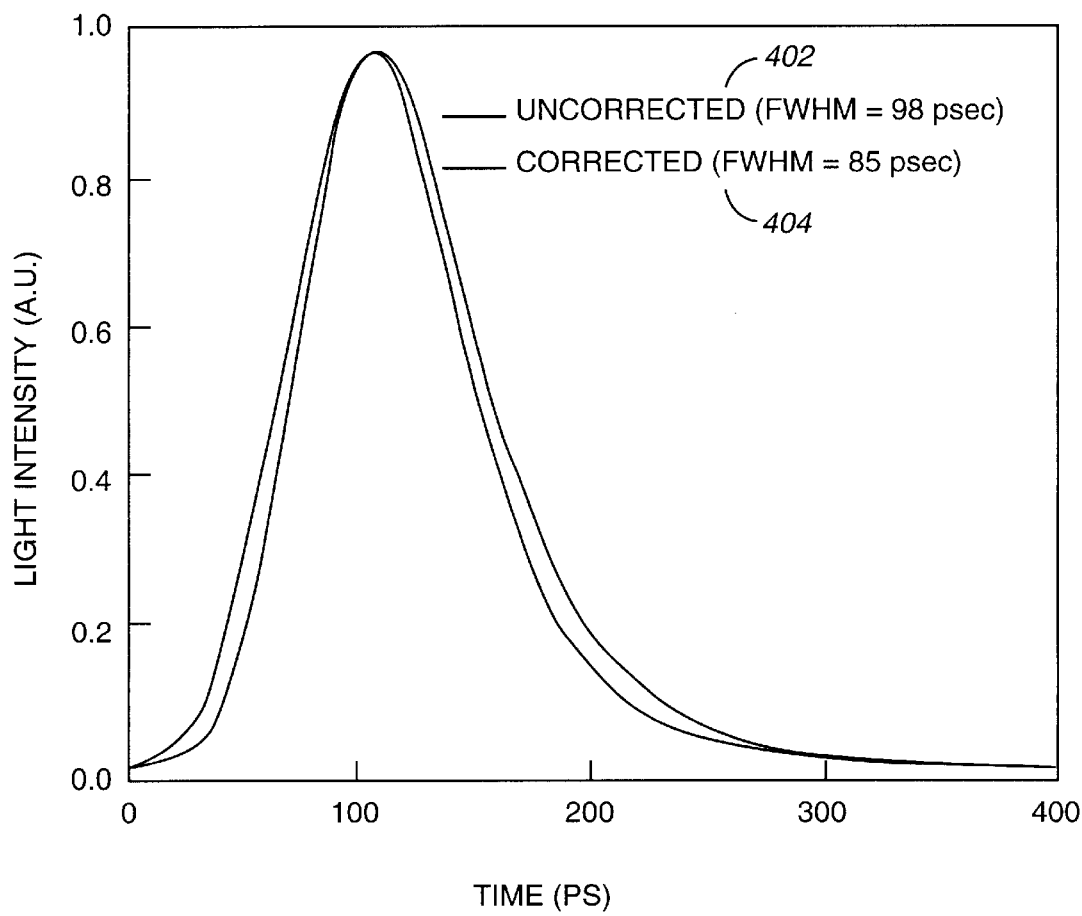
FIG. 4 shows two plots for photons detected for the overall system response of FIG. 1 according to the prior art ("uncorrected") and FIG. 2 according to the present invention ("corrected").

Turning now to FIG. 4, there are shown two histogram plots 400 for photons detected for the overall system 200 response of FIG. 2, which illustrates the improved timing in a TCPC system according to the present invention. The two plots 400 represent the uncorrected 402 and the corrected 404 curves of FIG. 4. A histogram of the digitized output of converter 108 (ignoring the pulse amplitude) gives the temporal response function of the conventional TCPC system (i.e., as in FIG. 1). This temporal response function is shown as the "uncorrected" histogram 402 in FIG. 4. The uncorrected histogram plot 402 is essentially derived by adding together all the curves of FIG. 3. The corrected histogram plot 404 is also a histogram of the digitized output of converter 108, but where the pulse amplitude associated with each photon is used to time shift each photon by the number of channels indicated in TABLE 1. Thus, the corrected histogram 404 is essentially derived by adding together all the curves of FIG. 3, but shifting each curve by the amount in Table 1, prior to adding where each digital channel of time corresponds to 7.235 psec. Note that these shifts are not linear in pulse amplitude, and designing an analog circuit to provide the same effect would be difficult (although, in principle, possible). Using inexpensive processing power and memory in digital computers or dedicated digital circuits to time shift the curves of FIG. 3 gives a simple and effective means to optimize the temporal response of any SPD such as a photomultiplier, an avalanche photodiode, or a scintillation detector) used in any TCPC system.

Note that the improvement in the full width at half maximum shown in the corrected histogram 404 in FIG. 4 is approximately 13% from the uncorrected histogram plot 402. This is a significant improvement in time resolution. For the correction shown in FIG. 4, only the pulse amplitude is used to determine how much to shift each photon in time. Several other improvements in the temporal response function can be realized by using other or additional criteria derived from the electrical pulse from the detector. One such additional first criteria for improving the temporal response when shifting the pulses by relative amplitude is using the slew rate of the pulse, which may be determined with two level triggers on the rising edge of the electrical pulse from the single photon detector SPD as explained in U.S. Pat. No. 3,676,783. Another possible second criterion for improving the temporal response when shifting the pulses by relative amplitude is a level trigger on the rising edge of the electrical pulse and a second level trigger on the falling edge of the pulse to determine the pulse width. Whichever criteria related to the electrical pulse from the detector are digitized and used to determine the shift time to be applied to the digital delay measurement prior to histogramming, the digital processing method disclosed here can be used to provide the best possible temporal response function.

Because of the ready availability of digital processing represented by such devices as personal computers, the time shifting described above is readily performed, as described above, by digital means. It will be readily apparent to one skilled in the art, however, that the time shifting can also be performed by analog means. The time shifting to be applied may be nonlinear in the chosen criteria, as is the case in TABLE 1, which could be difficult to implement in a purely analog system.

Moreover, using an imaging detector 106, such as the Mepsicron™, with this pulse shaping electronics 202 of FIG. 2 and the time shifting techniques above, the improved method of timing may be applied to each region of the active area of the detector separately, resulting in optimum timing from each such area. The data presented above were taken from a portion of about 4% of the area of a Mepsicron™ detector. Other areas of the detector were found to have slightly different characteristics, and would require a different correction for optimum time resolution.

Although a specific embodiment of the invention has been disclosed, it will be understood by those having skill in the art that changes can be made to this specific embodiment without departing from the spirit and scope of the invention. The scope of the invention is not to be restricted, therefore, to the specific embodiment, and it is intended that the appended claims cover any and all such applications, modifications, and embodiments within the scope of the present invention.

What is claimed is:

1. A system for time-correlated photon counting comprising:
at least one photon detector for producing electrical pulses corresponding to photons read from a target;
at least one converter comprising:
a first input coupled to a trigger output from a pulsed optical source;
a second input for receiving the electrical pulses;
digital delay measurement apparatus to measure the time difference between the trigger output and the electrical pulses;
at least one pulse shaping electronic circuit for receiving the electrical pulses and producing a series of one or more non-linear criteria;
a digitizer for digitizing one or more criteria related to the electrical pulses;
an interface to a storage device for storing the digital delay measurements and for storing the digitized criteria; and
means for time-shifting at least part of the stored digital delay measurements based on at least part of the stored digitized criteria so that the width of the temporal response function for the system is minimized.

2. The system according to claim 1, wherein one of the digitized criteria represents the integrated area of the electrical pulses.

3. The system according to claim 1, wherein one of the digitized criteria represents the time difference between two independent level triggers on the electrical pulses.

4. The system according to claim 1, wherein one digitized criterion represents the non-linear characteristic signals representing the constant fraction triggering of the electrical pulses.

5. The system according to claim 1, wherein one digitized criterion represents the non-linear characteristic signals representing the analog slew rate of the electrical pulses.

6. The system according to claim 1, wherein the detector has an active area and different portions of the active area have different time shift functions so that the width of the temporal response function of each portion is separately minimized.

7. The system according to claim 1, wherein the digital data is stored and processed in a multichannel analyzer.

8. The system according to claim 1, wherein the digital delay measurement is stored and processed in a digital computer.

9. The system according to claim 1, wherein the digital data delay measurement is stored and processed in a digital circuit specifically designed for such storage and processing.

10. The system according to claim 1, wherein the means for time-shifting comprises an analog electronic circuit.

11. A system for time-correlated photon counting comprising:
at least one photon detector for producing electrical pulses corresponding to photons read from a target;
at least one discriminator comprising:
a first input coupled to a trigger output from a pulsed optical source;
a second input for receiving the electrical pulses;
a time-to-pulse height converter for producing a series of difference signals each with a respective maxima and whose magnitude is related to the time difference between the trigger output and the electrical pulses;
at least one pulse shaping electronic circuit for receiving the electrical pulses and producing a series of one or more non-linear characteristic signals with a maxima in response thereto;
an analog-to-digital converter with a first input for receiving at least part of the difference signals and a second input for receiving at least part of the non-linear characteristic signals and for producing a first series of digital signals representing the difference signals and a second series of digital signals representing the non-linear characteristics signals; and
an interface to a multichannel analyzer for time-shifting at least part of the first series of digital signals based on at least part of the second series of digital signals so that the maxima for any given difference signals occur at the same time as the maxima for at least one other part of the series of difference signals.

12. A method for time-correlated photon counting comprising the steps of:
producing electrical pulses from at least one photon detector corresponding to photons read from a target;
coupling a first input on a converter to a trigger output from a pulsed optical source;
receiving on a second input of the converter the electrical pulses;
measuring on the digital delay measurement apparatus the time difference between the trigger output and the electrical pulses;
producing a series of one or more non-linear criteria with at least one pulse shaping electronic circuit for receiving the electrical pulses;
digitizing one or more criteria related to the electrical pulse;
coupling a storage device for storing the digital delay measurements and for storing the digitized criterion; and
time-shifting at least part of the stored digital delay measurements based on at least part of the stored digitized criterion so that the width of the temporal response function for the system is minimized.

13. The method according to claim 12, wherein the step of digitizing one or more digitized criteria includes digitizing the integrated area of the electrical pulses.

14. The method according to claim 12, wherein the step of digitizing one or more criteria includes digitizing the time difference between two independent level triggers on the electrical pulses.

15. The method according to claim 12, wherein the step of digitizing criterion includes digitizing the non-linear characteristic signals representing the constant fraction triggering of the electrical pulses.

16. The method according to claim 12, wherein the step of digitizing one or more criteria includes the digitizing the non-linear characteristic signals representing the analog slew rate of the electrical pulses.

17. The method according to claim 12, wherein the step of producing electrical pulses includes producing electrical pulses from an active area of the detector and different portions of the active area have different time shift functions so that the width of the temporal response function of each portion is separately minimized.

18. The method according to claim 12, wherein the step of coupling to a storage device includes coupling to a multichannel analyzer.

19. The method according to claim 12, wherein the step of coupling to a storage device includes coupling to a digital computer and the step of time-shifting occurs in the digital computer.

20. The method according to claim 12, wherein the step of coupling to a storage device includes coupling to a digital circuit and the step of time-shifting occurs in the digital circuit.

21. The method according to claim 12, wherein the step of time-shifting includes time-shifting with an analog electronic circuit.

* * * * *